United States Patent [19]

Beu

[11] 4,323,346
[45] Apr. 6, 1982

[54] DENTAL ARTICULATOR
[75] Inventor: Richard A. Beu, Eggertsville, N.Y.
[73] Assignee: Teledyne Hanau, a division of Teledyne, Inc., Buffalo, N.Y.
[21] Appl. No.: 111,020
[22] Filed: Jan. 10, 1980
[51] Int. Cl.³ .............................................. A61C 11/00
[52] U.S. Cl. ........................................ 433/58; 433/66
[58] Field of Search ..................... 433/58, 57, 54, 61, 433/64, 66

[56] References Cited

U.S. PATENT DOCUMENTS

| | | | |
|---|---|---|---|
| 396,566 | 1/1889 | Hayes | 433/58 |
| 870,909 | 11/1907 | Snow | 433/58 |
| 1,341,191 | 5/1920 | Nakahara | 433/58 |
| 1,452,477 | 4/1923 | Chott | 433/58 |
| 1,711,019 | 4/1929 | Gambill | 433/58 |
| 2,119,896 | 6/1938 | Van Dorn et al. | 433/57 |
| 2,474,488 | 6/1949 | Moore | 433/57 |
| 2,571,280 | 10/1951 | Naggi | 433/58 |
| 2,982,025 | 5/1961 | Page | 433/57 |
| 3,073,030 | 1/1963 | Gibson et al. | 433/58 |
| 3,624,906 | 12/1971 | Granger | 433/57 |
| 3,905,112 | 9/1975 | Swanson | 433/57 |
| 3,965,576 | 6/1976 | Eveland | 433/58 |
| 4,260,377 | 4/1981 | Hobo et al. | 433/58 |

FOREIGN PATENT DOCUMENTS 2915925 10/1979 Fed. Rep. of Germany ........ 433/58

Primary Examiner—Gene Mancene
Assistant Examiner—John J. Wilson
Attorney, Agent, or Firm—Raymond F. Kramer

[57] ABSTRACT

A dental articulator of simplified structure, capable of relatively forward and sideward movements to simulate human jaw movements, includes component parts representing lower jaw and maxillary structures held together at simulated condylar joints, wherein spring means press simulated condyles against matching condylar joint walls to hold them in such position when desired and disengaging means are provided which, when actuated, move the spring means away from the associated condyle part, facilitating relative movement of the simulated jaw parts at such joint. When both ends of the spring are moved away from the condyles the jaw portions of the articulator may be separated so that examination of the wear surfaces of dentures held therein may be effected easily. Specifically preferred structural features of the present articulator include a flat spring in strip form, bent at both ends thereof to form anterior condylar joint walls which yieldably hold the simulated maxilla against the condyles, and dog means, near both spring means ends, for selectively moving said spring ends away from the condyles and holding them in such position out of contact with the condyles, and for selectively allowing such spring ends to press against the condyles, as desired.

6 Claims, 9 Drawing Figures

DENTAL ARTICULATOR

This invention relates to dental articulators. More particularly, it relates to a simple and economical articulator wherein resilient means are used to press simulated condyles against simulated fossae and means are provided to move the resilient means so that, when desired, they are held in open position, wherein they do not press a condyle or the condyles against such fossa or fossae and are not in contact with such condyle(s).

Dental articulators of various types have been in use for many years. Such articulators usually include simulated lower jaw and maxillary portions to which plaster mounts for synthetic organic polymeric materials, molded to imitate palate and gums, may be held, and to which artificial gums, artificial teeth may be fastened. The upper and lower structures of the articulator are desirably relatively movable in such manner as to simulate human jaw movements. To effect this a simulated condylar joint may be produced, utilizing spherical knobs representing human condyles, and simulated condylar joints, imitating the fossae. Various types of simulated condylar joints, some with movable superior, posterior and medial fossae walls and others with stationary such walls, have been suggested. Some such structures are very complex, closely imitating the human condylar joint, and capable of being varied so that such imitation may be exceedingly accurate. Others, such as that described in U.S. Pat. No. 3,769,708, imitate an average human joint structure. While the former are more accurate, they are more expensive to manufacture and are more complicated to use. The simpler or average structures, while cheaper, are often inadequate. Especially with simpler articulators, means for satisfactorily and quickly engaging and disengaging the upper and lower articulator sections have not been provided. The spring-dog combination engaging-disengaging means of the present invention are not shown or suggested in the prior art known to applicant. U.S. Pat. Nos. 396,566; 1,341,191; 1,452,477; 2,571,280; and 3,965,576 are representative of the closest prior art known to applicant in which springs have been employed in articulators, although in manners different from that of his invention.

The present invention allows for a satisfactory simulation of condylar joint movement, permitting the imitation of forward and sideward jaw movements so that the dental laboratory technician and dentists can easily check the fits of dentures and artificial teeth in the laboratory, before installation in the patient's mouth. An important aspect of this invention is in the ready removability of the simulated maxilla from the lower jaw portion of the articulator by controlled removal of the spring means of this invention from contact with the condyles. Another important feature is the simple holding means provided for desirably pressing the spherical condyles against the superior, posterior and medial walls of the fossae in a desired direction, against the "corner" where such walls converge or meet. Of course, this may be considered as the holding means acting to draw the simulated fossae walls forward against the condylar globes. Such useful effects are obtained by means of a simple spring strip, which is so shaped and positioned as to be easily mounted to effect the desired biasing of the condyles against the simulated fossae. Furthermore, such bias may be relieved and the spring may readily be held in open position by a sturdy and foolproof mechanism, to facilitate separation of the articulator parts, when desired.

In accordance with the present invention, in a dental articulator for simulating relative jaw and tooth movements, which includes a pair of simulated condyles on a lower mounting means which simulates a part of a lower jaw, and a simulated maxilla, mountable on the condyles and movable with respect to the condyles to simulate forward and sideward jaw movements, an improvement comprises resilient means for yieldably holding the simulated maxilla against the condyles and means for moving said resilient means out of contact with either or both of said condyles, as desired, so as to facilitate movement of the simulated maxillary portion of the articulator and, when both condyles are disengaged from said resilient means, facilitating removal of the maxillary portion from the lower jaw portion of the articulator. In preferred embodiments of the invention, as will be apparent from this description and the accompanying drawing, the resilient means is a thin flat strip of spring steel, suitably bent at the ends thereof, and the means for providing for engagement or disengagement of the spring contact with the condyles are a pair of rotatable dogs, each having a flat side bearable against the flat spring to hold it in a set opened position, when desired, and permitting "closing" of the spring and pressing against the associated condyles, when desired.

One aspect of the invention, as claimed, is that in a dental articulator for simulating relative jaw and tooth movements, which includes a pair of simulated condyles on a lower mounting means which simulates a part of a lower jaw, and a simulated maxilla, mountable on the condyles and movable with respect to the condyles to simulate forward and sideward jaw movements, which maxilla, where it is mountable on the condyles, includes medial, superior and posterior joint walls so shaped as to simulate fossae, an improvement comprises a flat spring in strip form, bent at the ends thereof to form anterior condylar joint walls, which ends yieldably hold the simulated maxilla against the condyles, and in which means are provided, near both spring ends, for selectively moving said spring ends away from the condyles and holding them in such position out of contact with the condyles, and for selectively allowing said spring ends to press against the condyles. Another feature of this invention resides in the provision in a dental articulator for simulating relative jaw and tooth movements, which includes a pair of simulated condyles on a lower mounting means which simulates a part of a lower jaw, and a simulated maxilla, mountable on the condyles and movable with respect to the condyles to simulate forward and sideward jaw movements, an improvement which comprises a flat spring having ends thereof in contact with the condyles and yieldably holding the simulated maxilla against them, which ends are selectively disengageable from said condyles, and a pair of separate dog members for selectively moving said spring ends out of contact with the associated condyles to facilitate desired relative jaw movements and, when both condyles are disengaged from said spring ends, facilitating removal of the maxilla from the lower jaw part of the articulator, which dog members each have a side bearable against a portion of the flat spring to hold it in said open position, in which it does not press against the associated condyle.

The invention will be readily understood from the accompanying description thereof, taken in conjunction with the drawing, in which.

Figure 1:
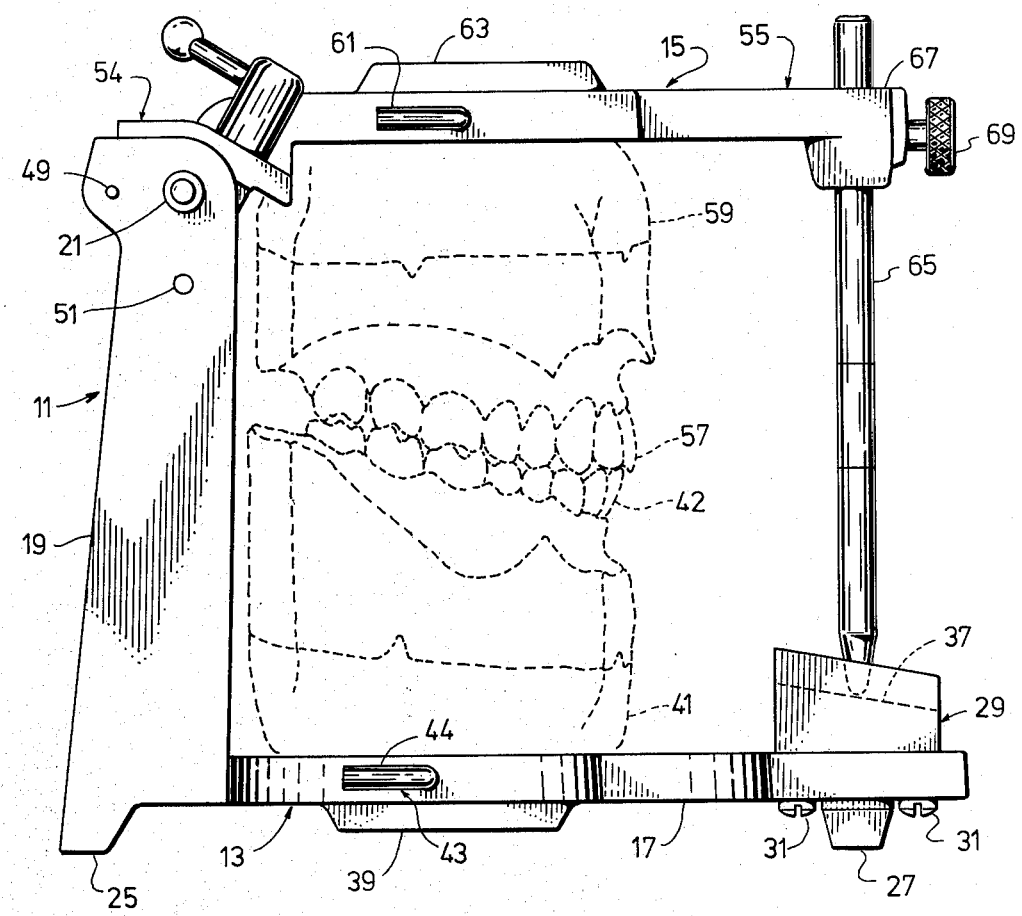
FIG. 1 is a side elevational view of the articulator of this invention, with mounting plaster and full lower and upper dentures (shown in phantom) held in position thereon.

In FIG. 1 articulator 11 is shown with lower jaw part 13 and simulated maxilla portion 15 in closed centric position. Part 13 includes a base portion 17 and vertical supports 19, in which supports there are mounted stepped cylindrical shafts 21 for holding simulated condyles 23 (clearly shown in FIGS. 2-5), which are rotatable about the shaft axes. (It will be noted that corresponding, matching or symmetrical parts may be identified herein by the same numeral, which practice helps to limit the presence of an obscuring number of numerals on the drawing). Shafts 21 are adapted to have mounted thereon the corresponding portions of a face-bow, for use in a manner known in the art. Base 17 is supported on three legs, two of which, identified by numeral 25, are integral parts of the simulated lower jaw part 13 of the articulator, and one of which, 27, is a part of the incisal rod guide member 29, held to the forward part of the lower articulator member base 17 by screws 31. Guide 29, as better shown in FIG. 2, includes downwardly, inwardly and forwardly slanted surfaces 33 and 35, which meet at line 37, which serve as a guide for the incisal rod and for controlling relative movements of the simulated maxilla and lower jaw during movements intended to simulate forward and sideward movements of a particular human lower jaw. Walls 34 and 36 limit movement of rod 65.

Figure 2:
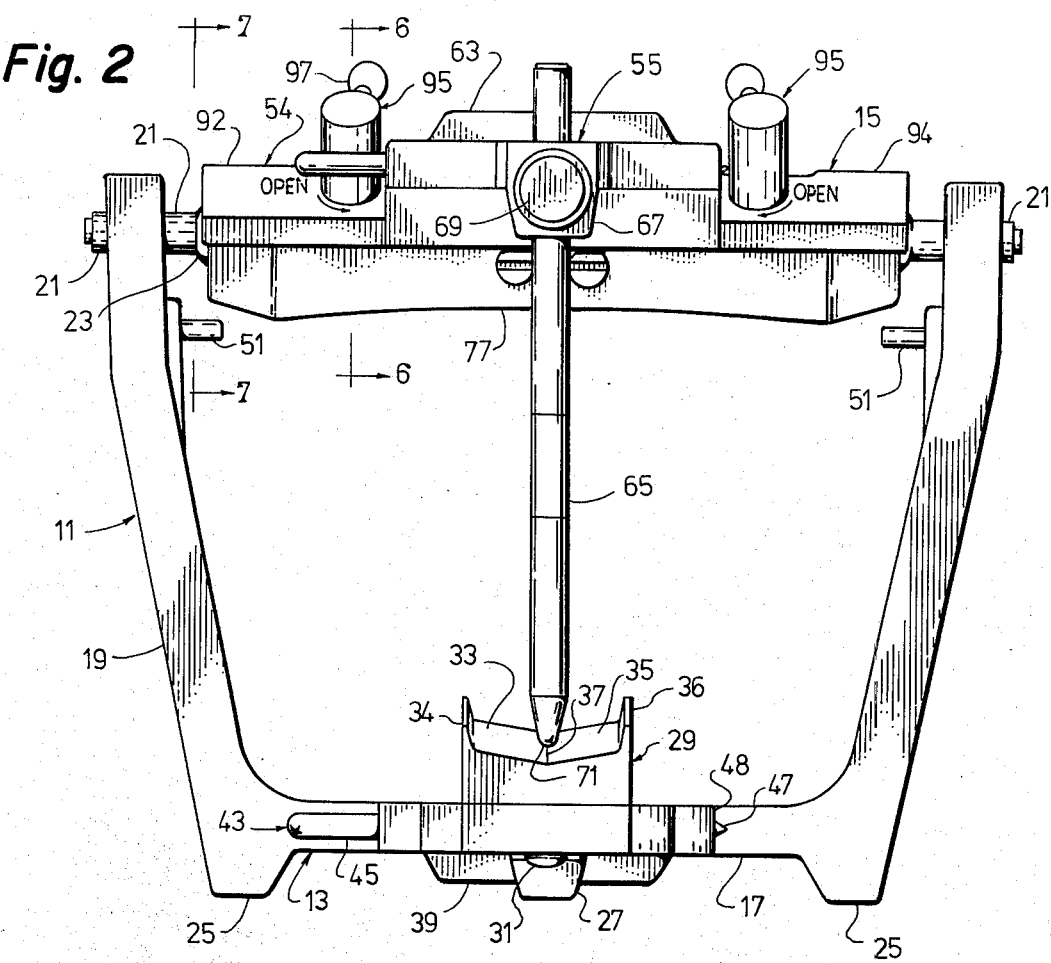
FIG. 2 is a front elevational view of such articulator, in closed position.
Figure 3:
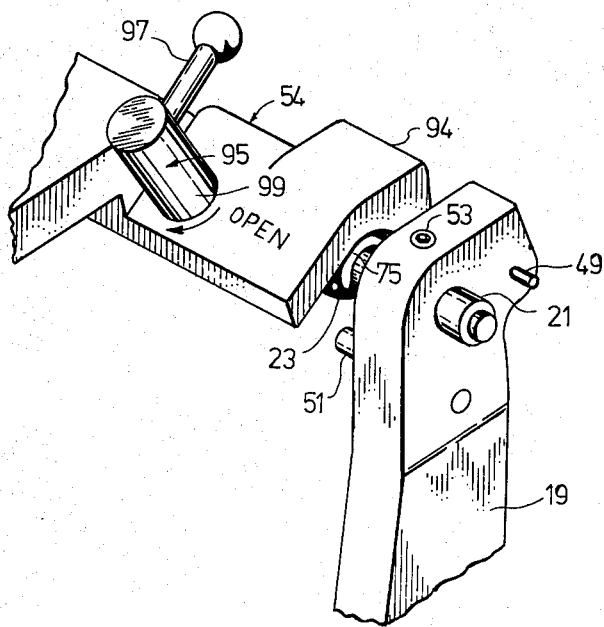
FIG. 3 is an enlarged perspective view of a part of the articulator of FIG. 2.
Figure 4:
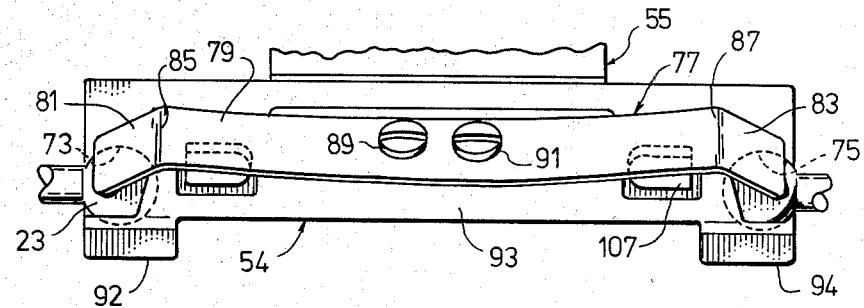
FIG. 4 is a bottom plan view of a portion of the maxillary part of the articulator held in position on the simulated condyles of the lower jaw portion thereof, with the condylar joints being in "closed" position.
Figure 5:
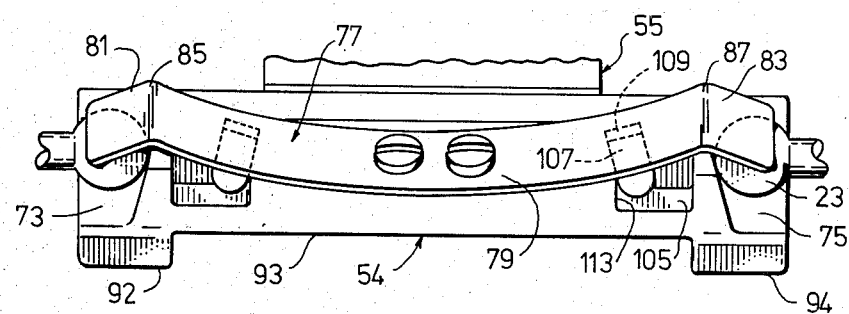
FIG. 5 is a view corresponding to FIG. 4 but with the resilient means thereof, which normally holds the condylar joints in closed position, being biased open.
Figure 8:
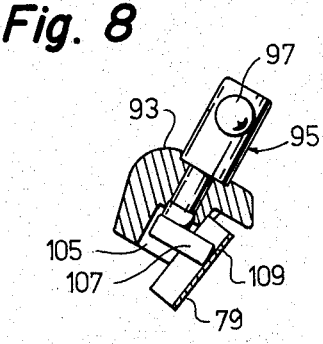
FIG. 8 is a sectional view corresponding to FIG. 6 but taken with the spring biasing mechanism in open position.

Depression 39 includes within it a hollow, not clearly shown but known to one of skill in the art, for supporting a corresponding shape of plaster construction 41, holding denture 42, which plaster part is additionally firmly held in place by pin 43, the handle portion of which is designated by numeral 44, in FIG. 1. In FIG. 2 are shown pin portion 45 and point 47 of the pin, extending beyond a wall 48 of base 17, and frictionally holding to an opening therein by means of the taper of the point. Near the top of vertical supports 19, on the same level as stepped cylindrical shafts 21, are located pins 49, shown in FIGS. 1 and 3, the axes of which are 12 mm. behind the corresponding axes of the face bow mounting shafts 21. 12 Mm. corresponds to the distance between the external auditory meatus and the human condyle, on the average, and pins 49 are adapted for use with some face bows. Stops 51 are cylinders, rods or ferrules held in place in holes in vertical supports 19, and are adapted to prevent excessive backward movement of simulated maxillary member 15 during use of the articulator. Such stop pins, as illustrated, include synthetic organic polymeric plastic sleeve portions, preferably of polypropylene, polyethylene or nylon, to cushion any shocks, to deaden sound and to prevent wear of the contacting parts. As is better seen in FIG. 3, the location of the simulated condyles 23 may be modified, so as to control the intercondylar distance, by means of set screws 53 or similar holding means.

Maxillary portion 15 of the present articulator includes most of the novel structure of the present invention, apart from the simulated condyles. Somewhat like the previously described lower jaw part 13, simulated maxilla 15 includes a posterior transverse or sidewardly extending portion 54 and a longitudinal or forwardly extending portion 55. The forward part includes the more conventional articulator structure and the posterior or transverse part includes the condylar joints or simulated fossae and the unique mounting means of the present invention, which allows ready removal of the maxillary portion of the articulator when desired, while still permitting the simulation of realistic relative jaw movements. Upper denture 57, held to plaster part 59, is joined to longitudinal part 55 of maxilla 15 by means of pin 61 passing through plaster 59, which fits in a recess, not clearly shown, although its location is evident, in extended portion 63, in a manner like that described with respect to the lower portion of the articulator. At the forward part of the longitudinal upper section of the articulator, incisal pin 65 is held in desired position in mounting section 67 by thumb screw 69, so that the round pointed lower end 71 of the incisal rod, resting on an upper portion of incisal guide 29, in conjunction with the fossae-condyle contacts, supports the maxillary part 15 of the articulator.

In FIGS. 1-4 the articulator parts thereof are shown in centric position, with condyles 23 being held tightly against simulated fossae 73 and 75, located at ends 92 and 94 of a transverse part 54 of the articulator maxilla. The superior, medial and posterior wall portions of the fossae have not been specifically indicated in the drawing, to avoid confusion of parts, but to those of skill in the art the location thereof will be clear and this discussion will be easily understood. In the present articulator, so that the movements thereof may simulate relative movements of the human jaw, it is important that the simulated fossae resemble those of the human jaw, and therefore the shapings of the superior, medial and posterior walls of the simulated fossae should be like those of the human condylar joint fossae and the condyles should ride against such walls in manner similar to human condyle-fossa movements. Desirably, the condyles should be pressed against the areas of convergence of the mentioned walls and such is effected in the present articulator.

Although the condyles are urged relatively against the convergences of the fossae walls they should be free to move (actually, in the articulator the maxillary portion containing the fossae moves but the relative result is the same) along such walls, following paths simulating those of normal jaw movements. This is possible with the present articulator structure in which resilient means 77 urges the condyles against the fossae walls. Resilient means 77, preferably a thin, flat, strip spring, such as one of spring steel or plated flexible metal, e.g., chrome plated spring brass, is desirably bent at both ends 81 and 83 thereof, preferably at an angle of about 20° to 40°, e.g., 30°, so as to urge or bias the condyles against the mentioned corners of the fossae. However, although ends 81 and 83 of resilient means 77 do so urge the condyles, movement away from such corner and along the appropriate walls is possible and is effectable to simulate human jaw movements.

Resilient means 77 includes a central or medial portion 79 between ends 81 and 83 and bends or bend lines 85 and 87 respectively, which separate such medial portion from such ends. Normally such bends are transverse but they may be at another angle, e.g., 80° to 100° to the longitudinal, when desired. Spring means 77 is held to a central portion 93 of transverse part 54 of maxilla 15 by screws 89 and 91 or other suitable, preferably similar, fastening means. It is preferable that two such screws or fastening means be utilized so as to hold the spring means in position, preventing twisting or turning thereof. Also, by choosing the locations of the screws, i.e., the distances from them to the spring bends, the spring tension or force exerted can be regulated, because this is a function of the spring characteristics of the material, the spring strip dimensions and the lever arm from holder to spring end portion.

While it is possible to utilize the articulator with the resilient means in position, as shown in FIGS. 1–4, moving the maxillary part backward and upward to simulate a forward lower jaw movement and moving it sideward to simulate corresponding opposite sideward lower jaw movements, against the forces of the spring ends on the condyles, it is sometimes desirable for such spring tension to be relaxed at one or both condylar joints. This allows more delicate relative movements of upper and lower denture parts with respect to each other. Also, when it is desired to disassemble the articulator so that a denture held to a portion thereof may be studied, such disassembly is preferably effected without having to force the resilient means open. Such forcing can cause slipping and damage to the denture. Accordingly, the means of the present invention, which moves the resilient means into a position facilitating ready movement of one or both condyles with respect to the associated fossae, allowing ready disassembly of the articulator, represents a useful and important advance in the articulator art.

As is apparent from the figures, the resilient means 77 may be moved out of contact with the condyles 23 by suitable engaging-disengaging means 95, which includes a handle 97, a body portion 99 a pin or journal portion 101, mounted for partial rotation in the bearing, passageway or opening 103 in the middle portion 93 of transverse part 54 of maxillary member 15. At the end of shaft 101 is a dog or toggle-type member 107 which is rotatable about a quarter of a turn or 105° so that a flat portion thereof 109 may bear against an adjacent portion of spring 77 and move it to open position, allowing freer condylar movement of the adjacent condyle. It will be noted that dog 107, in relaxed position, wherein the spring bears against the condyle, fits in recess 105 in transverse section 93 and in open position, wherein the flat face 109 thereof presses against the flat spring, the dog and spring surfaces substantially conform and the dog movement is inhibited by contact with recess wall 13, thereby effectively "locking" the resilient means in open position. In such open position the maxillary part of the articulator may be readily removed from the lower jaw part thereof and after study of the denture, modification thereof or other operation, may be replaced, after which, if desired, the respective handles may be moved and the ends of the resilient means or the anterior portions of the fossae may be again brought into contact with the condyles.

Figure 6:
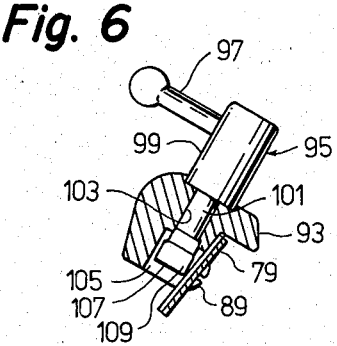
FIG. 6 is a partially sectional view of the spring and spring biasing means in closed position, taken along plane 6—6 of FIG. 2.
Figure 9:
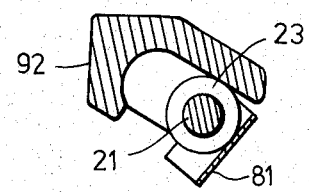
FIG. 9 is a sectional view corresponding to FIG. 7 but taken in open position and with the condyle being shown moved out of its socket and against the spring.
Figure 7:
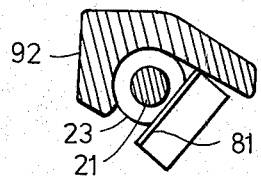
FIG. 7 is a corresponding sectional view taken along plane 7—7 of FIG. 2.

FIGS. 6–9 further illustrate the respective positions of the means for holding the resilient means in open or closed position. As shown in FIGS. 6 and 7 the means are in closed position and in FIGS. 8 and 9 they are in open position. It is not thought that further discussion of these figures is necessary because the parts thereof and their operations have previously been described with respect to the other illustrations.

The construction of the articulator and the workings thereof have been described and various advantages have been pointed out in the foregoing description. However, setting up and using the articulator will next be referred to in some detail and additional advantages will be pointed out. First, the articulator may be disassembled into parts that are easy to pack and transport. Primarily, these will be the lower portion, simulating the lower jaw, the upper portion, simulating the maxilla, and the incisal pin. Of course, various other minor parts may be removed and the spring means may be disengaged but it is usually preferred for the incisal guide, the incisal rod tightening screw and the spring to remain installed during shipment before set-up, with the spring in relaxed position. It will be noted that from such position the spring must be distorted somewhat when the maxillary part is installed on the condyles. Also, because of the curved shape of the combination of superior and posterior fossae walls the spring holds the simulated maxilla firmly in position on the condyles, making it impossible to release it unintentionally. If desired, different sized maxillae may be employed to allow for different intercondylar distances and the condyles may be relocated accordingly. The simulated fossae walls are of fixed shapes, corresponding to average wall structures of the human fossae. The incisal guide employed includes built-in 10° angles for the planes thereof, which angle has been found to be representative and which results in useful approximations of jaw movements for most patients. After setting of the stone, plaster and dentures in position, according to methods known in the art, and after simple assembly of the articulator by opening the spring ends, placing the maxillary part in place and closing the spring ends by moving the handles from the marked open to closed positions, 90° nearer to the articulator longitudinal vertical axis, the various test movements of the dentures may be made and they may be adjusted or modified accordingly. During these operations the articulator may be repeatedly taken apart by moving the handles to open positions and lifting the maxillary portion. Reinstallation is just as simple. Thus, no strains are created and damage to the dentures during assembly and disassembly of the articulator is avoided.

It will be seen that the construction of the present articulator is simple, yet effective. The parts thereof are readily cleaned and serviced, if servicing is ever required. They are sturdy, readily manufacturable, easy to operate and functionally effective. The articulator is easily repaired, should anything go wrong and is capable of use with various types of equipment on the market, including a plurality of facebow designs. The parts of the articulator do not wear excessively, do not become dirty easily and are not so small as to be difficult to install, remove, clean and replace. The articulator may be manufactured economically and may be sold at a reasonable price because of the advantages recited, easy manufacturability, few complex or small parts, readily available materials and simple construction.

The invention has been described with respect to a preferred embodiment and illustrations thereof but is not to be limited to these because it is evident that one of skill in the art, with the present specification and drawings before him, will be able to utilize substitutes and equivalents without departing from the invention. For example, different types and different shapes of springs or resilient members may be utilized, providing that they tend to hold the condyles in position with respect to the fossae, and different types of dog, snap or toggle mechanisms or other means for selectively moving the spring into contacting and withdrawn positions may be employed. Also, helical or coil springs may be employed, strip springs may be of chrome plated spring steel or spring brass and single actuating means may move both strip spring ends simultaneously. Similarly, materials of construction may be changed, parts may be die cast, forged, cast or machined and may be made of any of various suitable metals or alloys, plated or unplated, such as aluminum, steel, stainless steel and brass, or of synthetic organic polymeric materials, e.g., nylon, fiberglass reinforced polyester, phenol formaldehyde, polypropylene, polyacetal, polytetrafluoroethylene and polyurethane, where suitable.

What is claimed is:

1. In a dental articulator for simulating relative jaw and tooth movements, which includes a pair of simulated condyles on a lower mounting means which simulates a part of a lower jaw, and a simulated maxilla, mountable on the condyles and movable with respect to the condyles to simulate forward and sideward jaw movements, which maxilla, where it is mountable on the condyles, includes medial, superior and posterior joint walls so shaped as to simulate fossae, an improvement which comprises a flat spring in strip form, bent at the ends thereof to form anterior condylar joint walls, which ends yieldably hold the simulated maxilla against the condyles, and in which means are provided, near both spring ends, for selectively moving said spring ends away from the condyles and holding them in such position out of contact with the condyles, and for selectively allowing said spring ends to press against the condyles.

2. In a dental articulator according to claim 1 the improvement in which the flat strip spring is mounted on the simulated maxillary structure at about a middle portion thereof and the means for disengaging the spring contact with the condyles are a pair of separate, rotatable dogs, each having a flat side bearable against the flat spring to hold it in a set open position in which it does not press against the associated condyle.

3. In a dental articulator according to claim 2 the improvement in which the condyles are rotatable to inhibit wear of the surfaces thereof during use, the flat strip spring is of protectively metal plated spring steel and the ends of the steel strip are at an angle such that when in contact with the condyles they press the condyles against the simulated medial, posterior and superior fossae walls in a direction toward the convergence thereof.

4. In a dental articulator for simulating relative jaw and tooth movements, which includes a pair of simulated condyles on a lower mounting means which simulates a part of a lower jaw, and a simulated maxilla, mountable on the condyles and movable with respect to the condyles to simulate forward and sideward jaw movements, the improvement which comprises a flat spring having ends thereof in contact with the condyles and yieldably holding the simulated maxilla against them, which ends are selectively disengageable from said condyles, and a pair of separate dog members for selectively moving said spring ends out of contact with the associated condyles to facilitate desired relative jaw movements and, when both condyles are disengaged from said spring ends, facilitating removal of the maxilla from the lower jaw part of the articulator, which dog members each have a side bearable against a portion of the flat spring to hold it in said open position, in which it does not press against the associated condyle.

5. A dental articulator for simulating relative jaw and tooth movements which comprises simulated upper and lower jaw structures movably mountable together by means of a pair of ball and socket joint means, wherein portions of said socket are resilient means adapted to selectively yieldably press said ball means against socket internal walls and adapted to be selectively moved away from and to be held away from said ball means, when desired, to facilitate relative movement between the simulated upper and lower jaw portions and, when said resilient means are removed from contact with the ball means of both ball and socket joints, to facilitate disengagement of the simulated jaw structures from each other, and wherein a pair of dogs, each having a side bearable against a portion of the resilient means to hold it in a set open position at which it does not press against the associated condyles, is provided, each adjacent the resilient means at each of the respective ball and socket joints to selectively move the resilient means away from the condyles and to hold such means in open position, and to permit the resilient means to selectively press against the condyles, as desired.

6. A dental articulator for simulating relative jaw and tooth movements which comprises simulated upper and lower jaw structures movably mountable together by means of a pair of ball and socket joint means, wherein portions of said sockets are end portions of a strip of spring steel adapted to selectively yieldably press said ball means, which are simulated condyles, against socket internal walls, which are condylar joint walls of simulated fossae, and adapted to be selectively moved away from and to be held away from said ball means, when desired, to facilitate relative movement between the simulated upper and lower jaw portions and, when said end portions of the strip of spring steel are removed from contact with the ball means of both ball and socket joints, to facilitate disengagement of the simulated jaw structures from each other, and wherein means are provided for moving the spring ends away from the ball means and into a held open position, which means are a pair of separately rotatable dogs, each having a flat side bearable against a portion of the spring steel strip to hold it in set open position, in which position it does not press against the ball means.

* * * * *